United States Patent [19]

Gugger et al.

[11] Patent Number: 5,702,752
[45] Date of Patent: Dec. 30, 1997

[54] PRODUCTION OF ISOFLAVONE ENRICHED FRACTIONS FROM SOY PROTEIN EXTRACTS

[75] Inventors: Eric T. Gugger; Daniel G. Dueppen, both of Decatur, Ill.

[73] Assignee: Archer Daniels Midland Company, Decatur, Ill.

[21] Appl. No.: 614,545

[22] Filed: Mar. 13, 1996

[51] Int. Cl.$^6$ .................................................. A23L 1/20
[52] U.S. Cl. .................. 426/634; 426/429; 426/431; 426/490; 426/520
[58] Field of Search .................................. 426/634, 648, 426/429, 431, 443, 478, 490, 492, 520

[56] References Cited

U.S. PATENT DOCUMENTS

| | | | |
|---|---|---|---|
| 4,157,984 | 6/1979 | Zilliken | 252/407 |
| 4,232,122 | 11/1980 | Zilliken | 426/546 X |
| 4,264,509 | 4/1981 | Zilliken | 260/345.2 |
| 4,366,082 | 12/1982 | Zilliken | 252/404 |
| 4,366,248 | 12/1982 | Zilliken | 435/125 |
| 4,390,559 | 6/1983 | Zilliken | 426/545 |
| 4,883,788 | 11/1989 | Day et al. | 514/57 |
| 5,141,746 | 8/1992 | Fleury et al. | 424/195.1 |
| 5,424,331 | 6/1995 | Shlyankevich | 514/456 |
| 5,506,211 | 4/1996 | Barnes et al. | 514/27 |
| 5,554,519 | 9/1996 | Weber et al. | 435/125 |

FOREIGN PATENT DOCUMENTS

| | | |
|---|---|---|
| 95/10512 | 4/1995 | WIPO. |
| 95/10529 | 4/1995 | WIPO. |
| 95/10530 | 4/1995 | WIPO. |

OTHER PUBLICATIONS

Walz, "Isoflavon–und Saponin–Glucoside in Soja hispida", Justus Liebigs Ann. Chem., vol. 489, pp. 118–155, 1931.
Walter, "Genistin (an Isoflavone Glucoside) and its Aglucone, Genistein, from Soybeans", The Journal of The American Chemical Society, vol. 63, pp. 3273–3276, 1941.
Kudou et al., "Malonyl Isoflavone Glycosides in Soybean Seeds (Glycine max Merril)", Agricultural and Biological Chemistry, vol. 55 (9), pp. 2227–2233.

*Primary Examiner*—Milton Cano
*Attorney, Agent, or Firm*—Laff, Whitesel, Conte & Saret Ltd.

[57] ABSTRACT

The temperature sensitive differential of the solubilities of isoflavones is used to separate them by heating an aqueous soy molasses feed stream. The temperature of the feed stream is increased to select isoflavone fractions. Then the heated feed stream is passed through an ultrafiltration membrane. The resulting permeate is cooled to crystallize the isoflavone fractions. Or, the permeate may be put through a resin adsorption process in a liquid-chromatography column to separate out the desired isoflavone fractions. Various processes are described for drying and recrystallizing the resulting isoflavone solids.

21 Claims, 3 Drawing Sheets

PRODUCTION OF ISOFLAVONE ENRICHED FRACTIONS FROM SOY PROTEIN EXTRACTS

The invention relates to a production of isoflavone rich process streams by a treatment of an aqueous alcohol extract of defatted soybean flakes.

BACKGROUND OF THE INVENTION

Isoflavones are a unique class of plant flavonoids that have a limited distribution in the plant kingdom and may be physically described as colorless, crystalline ketones. The most common and important dietary source of these isoflavones are soybeans which contain the following twelve isoflavone isomers: genistein, genistin, 6"-0-malonylgenistin, 6"-0-acetylgenistin; daidzein, daidzin, 6"-0-malonyldaidzin, 6"-0-acetylgenistin; glycitein, glycitin, 6"-0-malonylglycitin, 6"-0-acetylglycitin (Kudou, Agric. Biol. Chem. 1991, 55, 2227–2233). Ninety-seven to ninety-eight percent of the soybean isoflavones are in the glycosylated form.

Traditionally, individuals have been limited in their use of soy foods to increase their levels of dietary isoflavones because the number and variety of soy foods available in the U. S. marketplace is limited.

The isoflavone, genistin, was first isolated from soybean meal in 1931 by Walz (Justus Liebigs Ann. Chem 489, 118) and later confirmed in 1941 by Walter (J. Amer. Chem. Soc. 63, 3273). Patents have described the production of isoflavone enriched soy-protein products (WO 95/10512; WO 95/10529; WO 95/10530), genistin malonate and daidzin malonate (U.S. Pat. No. 5,141,746), pharmaceutical-type compositions containing isoflavones (U.S. Pat. Nos. 5,424,331; 4,883,788), and isolation and modification of isoflavones from tempeh (U.S. Pat. Nos. 4,390,559; 4,366,248; 4,366,082; 4,264,509; 4,232,122; 4,157,984). However, the present patent relates to the manufacture of highly enriched isoflavone products containing either a wide-range of soy isoflavones or highly-purified genistin gained from an ethanol extract of defatted soybean flakes.

Since coronary heart disease (CHD) is a leading cause of death, especially in the United States and other industrialized nations, an elevated total and LDL cholesterol levels are important risk factors affecting human health. In humans, soy protein products appear to lower serum total cholesterol levels by an average of about 9.3% and to lower low-density lipoprotein (LDL) cholesterol by an average of about 12.9% when consumed at an average intake level of 47 g soy protein per day (Anderson et al., NEJM, 333:276–282, 1995).

Isoflavones (Phytoestrogens) are implicated as a class of compounds in soy protein products which is at least partly responsible for this cholesterol-lowering effect in animals (Setchell, in McLachlan JA, ed. Estrogens in the Environment II:69–85, 1985). In addition, studies with primates suggest that soy isoflavones may account for up to about 60–70% of the hypocholesterolemic properties of soy protein (Anthony et al., Circulation, 90:Suppl:I-235. (abstract), 1994; Anthony et al., J. Nutr., 125:Suppl 3S:803S–804S. (abstract), 1995; Anthony et al., Circulation, 91:925. (abstract), 1995).

It has also been suggested that isoflavones have an ability to play a role in the prevention of certain cancers. Japanese women who have consumed diets rich in isoflavones appear to have a very low incidence of breast cancer (Adlercreutz et al., J. Nutr. 125:757S–770S, 1995). Soy products have also been shown to decrease mammary tumor formation or to inhibit mammary tumor progression in rat breast cancer models (Barnes et al., Clin. Biol. Res. 347:239–253; Hawrylewicz et al., J. Nutr. 121:1693–1698, 1991). Genistein has been shown to inhibit protein tyrosine kinase (Akiyama et al., J. Biol. Chem. 262:5592–5595, 1987), to inhibit angiogenesis (Fotsis et al., Proc. Natl. Acad. Sci. USA. 90:2690–2694, 1993), and to induce differentiation in several malignant cell lines (Peterson, J. Nutr. 125:784S–789S, 1995), all of which may be important risk factors in cancer development. Genistein and glycitein (Biochanin A) also appear to inhibit the growth of androgen-dependent and independent prostatic cancer cells in vitro (Peterson and Barnes, Prostate 22:335–345, 1993). Genistein may act as an antioxidant (Wei et al., Nutr. Cancer 20:1–12, 1993).

SUMMARY OF THE INVENTION

Accordingly, an object of this invention is to provide a convenient way for individuals to consume isoflavones either as a nutritional supplement or as an ingredient in more traditional types of food.

In light of the potentially positive role of isoflavones and particularly genistein in the prevention of human disease, an object of this invention is to isolate purified forms of genistin, such as the glycone form of genistein, with or without subsequent recrystallization as a further purification step.

Another object is to produce a product which is enriched in the entire range of soy isoflavones in order to provide isoflavone products for human diet supplementation or to enrich food products or food ingredients.

In keeping with an aspect of the invention, selected isoflavones are extracted based on the differentials of the solubilities of isoflavones in aqueous solutions. Alcohol is removed from an extract of defatted soybean flakes by evaporation. Then, the remaining aqueous solution is subjected to ultrafiltration (UF) at an elevated temperature in order to separate soluble isoflavones from other and insoluble materials. The UF permeate containing the soluble isoflavones may be treated in either one of two ways: 1) the permeate is treated with an adsorptive resin for enabling a recovery of a broad range of isoflavone isoforms while removing soluble sugars and salts; or 2) the permeate cools to promote a crystallization of genistin. Then, genistin is isolated in a highly purified form by either centrifugation or filtration. The genistin may be further purified by a subsequent recrystallization from aqueous alcohol solutions.

BRIEF DESCRIPTION OF DRAWINGS

These and other objects of this invention will become more apparent from the following specification taken with the attached drawings, in which.

DETAILED DESCRIPTION OF THE INVENTION

This invention employs methods based on the differential of solubilities of isoflavones in aqueous solutions. Genistin is the least water soluble of the isoflavone glycosides, is insoluble in cold water, and is only slightly soluble in hot water (FIG. 1).

Figure 1:
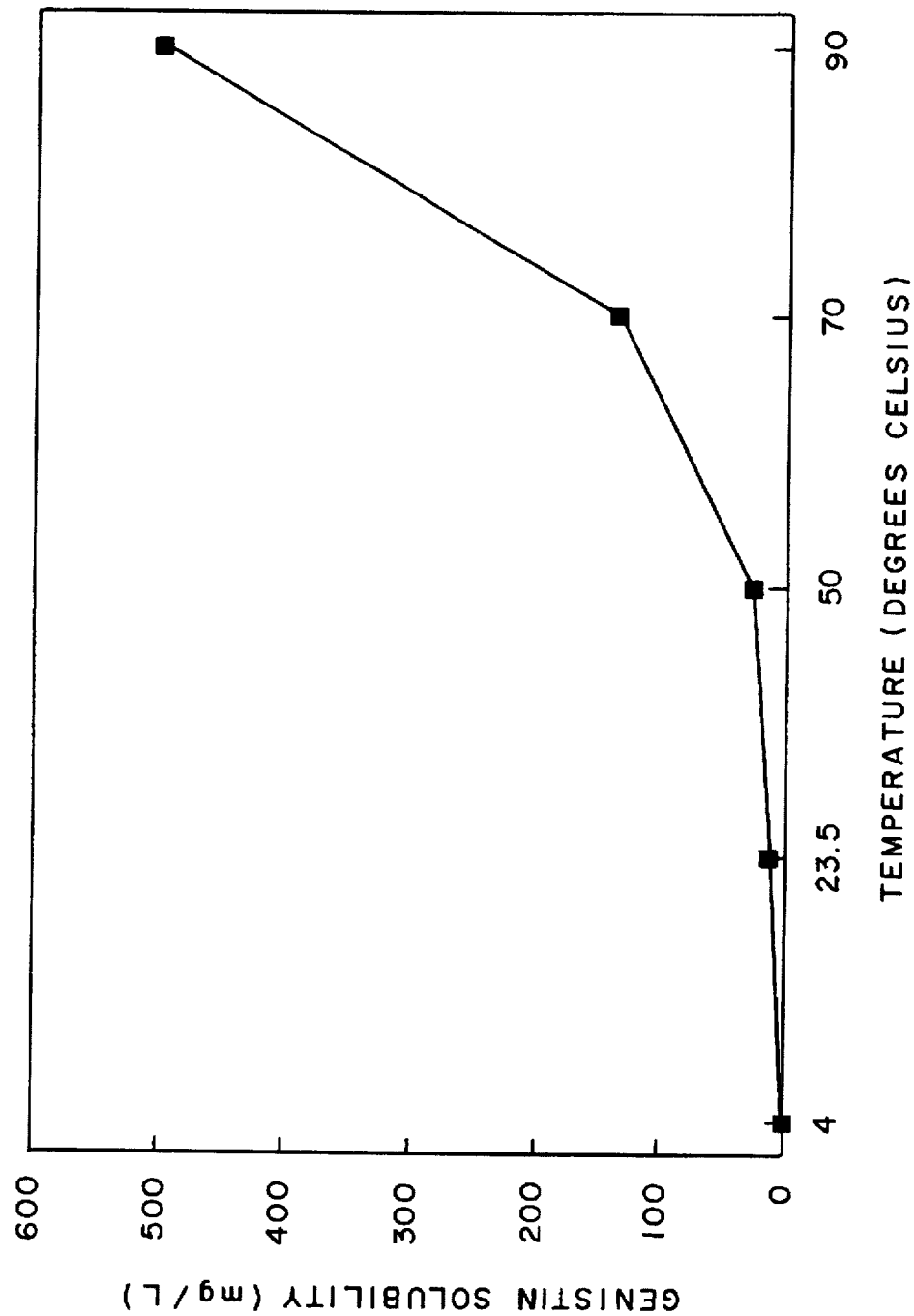
FIG. 1 is a graph showing the solubility of genistin in water vs. temperature.

In greater detail, FIG. 1 shows that the solubility of genistin is practically unchanged as the temperature increases from 4° C. to 50° C., but that the solubility increases rapidly as the temperature increases from 70° to 90° C. Therefore, if the manufacturing process is to recover genistin, the recovery step should be carried out at the high temperature end of the scale.

All isoflavone glycosides other than genistin have higher solubilities in water and readily pass through an ultrafiltration membrane, along with other water soluble components. By increasing the temperature of the aqueous solution prior to ultrafiltration, genistin and all other isoflavones can be separated from insoluble materials. The isoflavones in the ultrafiltration permeate can be recovered by treating the solution with a resin, washing the resin with water to remove soluble sugars, and eluting the isoflavones with a mixture of ethanol and water.

The starting material for the inventive processes is derived from an aqueous ethanol extract of hexanedefatted soybean flakes. The defatted soybean flakes are extracted with aqueous ethanol (approximately 60–80% ethanol by volume) at temperatures in the range about 44°–63° C. or 120°–150° F. This aqueous ethanol extract is then subjected to a vacuum distillation in order to remove ethanol. The alcohol-stripped extract is also known as "soy molasses" or "soy solubles."

Then the extract is adjusted within an appropriate temperature range (about 65°–95° C.) and subjected to ultrafiltration preferably by using a 10,000 molecular weight cut-off (MWCO) membrane. However, the process is not limited to this 10,000 cut-off membrane since any membrane which enables a filtration of the desired isoflavones may be used. The smallest cut-off membrane suitable for the inventive procedures should pass a molecular weight of 532, which provides a sufficient retention of insoluble material and passage of isoflavones.

Figure 2:
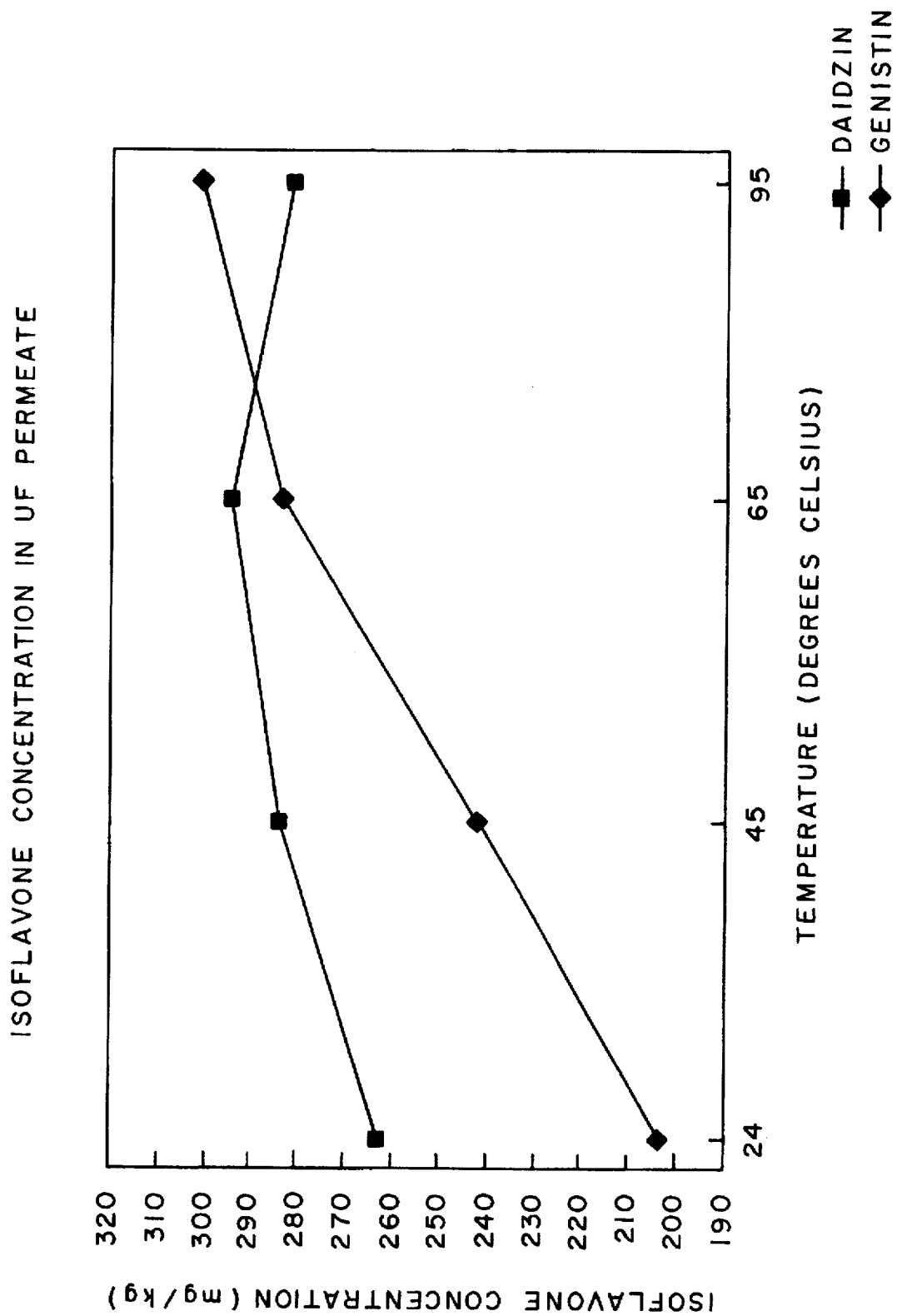
FIG. 2 is a graph showing the concentration of isoflavone in a UF permeate vs. temperature.

The effect of temperature on the concentration of two principle isoflavones, daidzin and genistin, in the UF permeate, is shown in FIG. 2. Cooler temperatures result in lower concentrations of genistin in the UF permeate. Daidzin concentrations are much less affected by temperature. To achieve optimal concentrations of isoflavones in the UF permeate, ultrafiltration should be carried out at a temperature above 65° C.

For example, FIG. 2 shows the differential between the concentration of daidzin and genistin in an aqueous solution permeate subjected to ultrafiltration. Ultrafiltration at 24° C. produces a high concentration of daidzin and a low concentration of genistin. Therefore, if the manufacturing step is to recover daidzin and reject genistin, perhaps the recovery should be carried out at the relatively low temperature of 24° C., although the exact temperature may be selected on a basis of how much genistin can be located in the permeate. On the other hand, if the manufacturing process is designed to recover both daidzin and genistin, perhaps it would be better to operate at the crossover point of about 78° C. For genistin, recovery should be carried out at a higher temperature.

Figure 3:
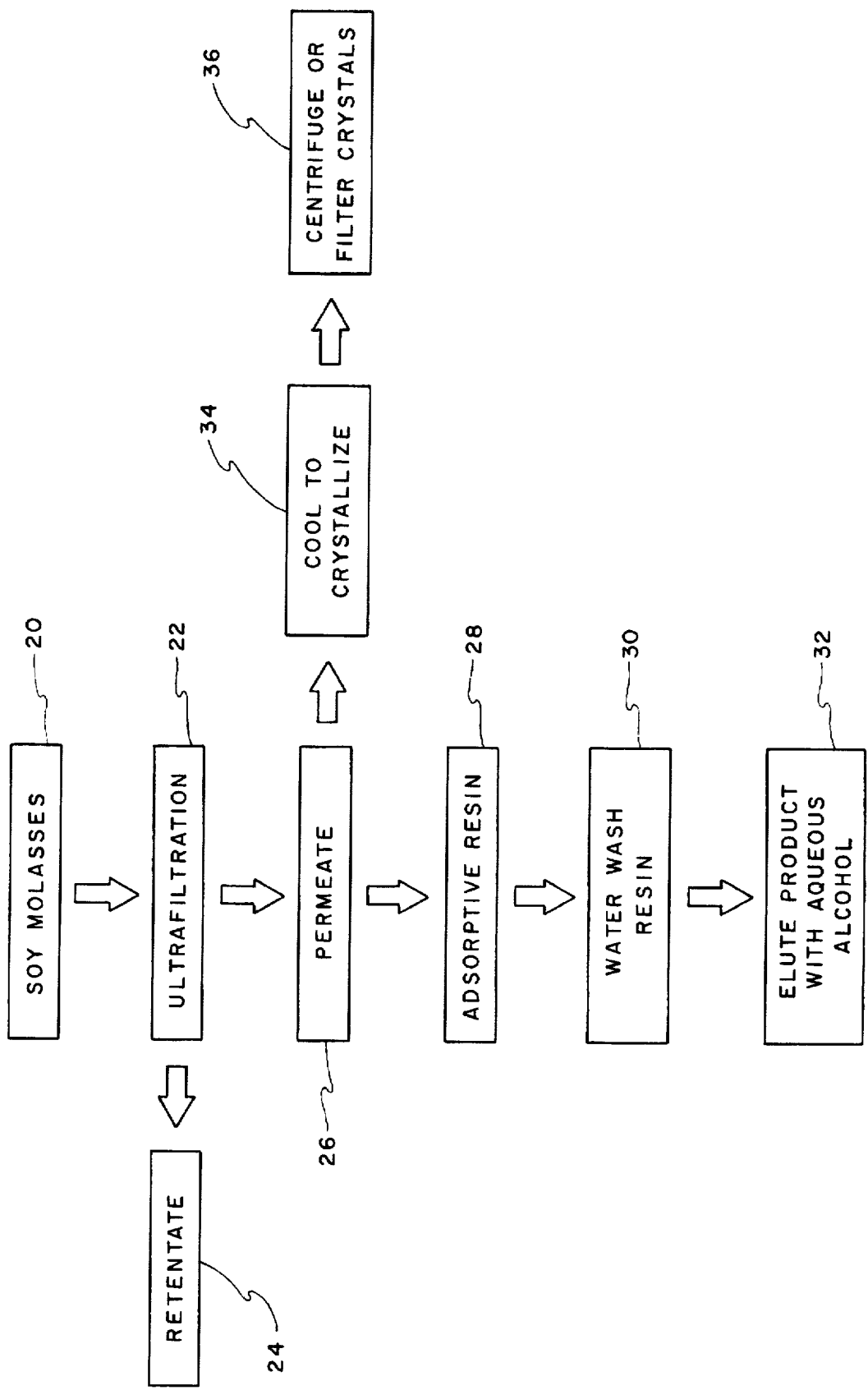
FIG. 3 is a process flow diagram showing the production of the inventive product.

A flow diagram representing one example of a manufacturing processes is shown in FIG. 3.

In greater detail, FIG. 3 shows at 20 that the preferred starting material is soy molasses which is subjected to ultrafiltration at 22. At 24, the retentate of the ultrafiltration is further processed, recycled, or otherwise used in another process.

If a batch type process is employed, the volume of the UF retentate fraction 24 is reduced during the ultrafiltration process by about one-third to two-thirds of the original alcohol-stripped extract volume, or stated otherwise is up to 12–15% solids. The UF retentate may be diafiltered with about one to three retentate volumes of water, which has been previously adjusted to be within a temperature range of about 65°–95° C. in order to recover a greater percentage of isoflavones in the permeate.

With or without the diafiltered permeate, the ultrafiltration permeate at 26 contains a variety of isoflavones and is adjusted to an appropriate temperature (45°–95° C.). Then, it is treated with an adsorptive resin at 28 in either a batch or chromatography column type process, followed by washing the resin with water at 30. Next, the isoflavones are eluted at 32 with aqueous alcohol (20–100% by volume, at 25°–85° C.) as either a gradient or single percentage process. The resulting material is dried (not shown in FIG. 3), preferably by evaporation, in order to produce a product which is approximately 30% isoflavones on a solids basis. The alcohol which is used at 32 may be ethanol, methanol, or isopropanol. The resin may be, but is not limited to, ethylvinylbenzene-divinylbenzene, styrene-divinylbenzene or polystyrene polymers, and may be either ionic or non-ionic.

Alternatively or in addition, with or without a diafiltered permeate, the ultrafiltration permeate 26 is adjusted to an appropriate temperature (about 4°–45° C.) in order to promote genistin crystallization at 34. Highly purified genistin crystals are then removed at 36 by a low-speed centrifugation or filtration and are finally washed with cold water (not shown in FIG. 3). The final product is between 70–90% pure genistin, measured on a dry basis. The genistin crystals can be further purified by recrystallization from aqueous alcohol solutions, such as aqueous ethanol, methanol, or isopropanol.

EXAMPLES

1) Ultrafiltration of Soy Solubles

Using a stainless steel steam-heated immersion coil, soy solubles (15.26 kg) were heated to a constant temperature of about 80° C. The soy solubles were then passed through a model 92-HFK-131-UYU spiral wound, polysulfone, 10,000 nominal molecular weight cut-off ultrafiltration membrane (Koch Membrane Systems, Inc., St. Charles, Ill.) by using a parastaltic pump. Back pressure on the exit side of the membrane was adjusted by means of a hand-tightened clamp to provide a permeate flow of 70 mL/minute. Ultrafiltration was continued until 9.4 kg of permeate was collected leaving 4.8 kg of retentate. Isoflavone profiles of the various fractions are shown below:

| Sample | Weight (kg) | % Solids | Total Isoflavones (g) | Genistin (g) | Daidzin (g) |
| --- | --- | --- | --- | --- | --- |
| Solubles | 15.26 | 8.65 | 11.45 | 4.01 | 4.30 |
| Retentate | 4.8 | 11.5 | 4.63 | 1.75 | 1.67 |
| Permeate | 9.4 | 7.7 | 6.6 | 2.29 | 2.68 |

2) Diafiltration of UF Retentate

Ultrafiltration retentate (80° C. initial temperature) was subjected to ultrafiltration as described in Example 1, except that 4.8 kg of tap water (25° C.) was fed into the retentate at a feed rate which is the same as the permeate rate or flux of the permeate that was being produced. The retentate was then further ultrafiltered to a final weight of 1.93 kg.

Isoflavone profiles of the various fractions is shown below:

| Sample | Weight (kg) | % Solids | Total Isoflavones (g) | Genistin (g) | Daidzin (g) |
|---|---|---|---|---|---|
| Retentate | 4.8 | 11.5 | 4.63 | 1.75 | 1.67 |
| Diafilt. Permeate | 7.25 | 4.28 | 2.12 | 0.72 | 0.96 |
| Diafilt. Retentate | 1.93 | 12.26 | 2.14 | 0.91 | 0.58 |

3) Adsorption and Recovery of Isoflavones From a Resin

A glass liquid-chromatography column (2.54 cm i.d.) was slurry packed in 70% ethanol with Dow XUS 40323 divinylbenzene, ethylvinylbenzene copolymer resin. The resin was cleaned with an additional 500 mL of 70% wt ethanol followed by 0.1% wt NaOH (500 mL) and water (500 mL). The resin was then back-flushed with water until the resin bed volume had expanded by about one half of its originally packed volume in order to partition the resin by size. The final packed volume was 100 mL. Fresh UF permeate (2000 mL or 20 column volumes) at an initial temperature of 60° C. was fed through the resin bed at 6 column volumes/hour or 10 mL/minute. The resin bed was washed with 500 mL of water at 10 mL/minute to remove residual sugars and other impurities. Isoflavones were then eluted from the resin with a linear gradient of 20–95% ethanol (500 mL total) at 10 mL/minute. Next, the entire ethanolic isoflavone containing fraction was vacuum dried to obtain a product with the following profile:

| Sample | Weight (g) | Total Isoflavones (g) | Genistin (g) | Daidzin (g) |
|---|---|---|---|---|
| Column Product | 6.56 | 2.2 | 0.92 | 0.83 |

4) Precipitation of Genistin From UF Permeate

A 7.69 kg volume of ultrafiltration permeate (85° C. initial temperature) was allowed to cool gradually to an ambient temperature (22° C.) during a 16 hour period, with constant stirring. The cooled permeate was then centrifuged at 900×g for 10 minutes in order to pelletize the genistin precipitate. The supernatant was poured off. The white pellet was diluted with water (100 mL) and recentrifuged at 900×g for 10 minutes in order to remove any residual supernatant. The white pellet was then vacuum dried to produce 1.02 g of a dried powder. The isoflavone composition of the dried powder was as follows:

| Sample | Weight (g) | Total Isoflavones (g) | Genistin (g) | Daidzin (g) |
|---|---|---|---|---|
| Genistin Precipitate | 1.02 | 1.00 | 0.77 | 0.17 |

5) Recrystallization of Genistin From UF Permeate Precipitate

A volume of 80% ethanol (50 mL) was slowly added to 1 g of permeate precipitate while refluxing until the precipitate dissolved. Then, the solution was filtered through Whatman 42 filter paper and slowly cooled (22° C.) to produce fine yellow-white crystals. The crystals were harvested by centrifugation at 900×G for 10 minutes. The supernatant was poured off. Next, the crystals were mixed with 50 mL of water (4° C.) and recentrifuged to remove any residual supernatant. The water was then poured off and the crystals were vacuum dried to produce a product with the following isoflavone profile:

| Sample | Weight (g) | Total Isoflavones (g) | Genistin (g) | Daidzin (g) |
|---|---|---|---|---|
| Genistin Crystals | 0.52 | 0.52 | 0.45 | 0.05 |

Those who are skilled in the art will readily perceive how to modify the invention. Therefore, the appended claims are to be construed to cover all equivalent structures which fall within the true scope and spirit of the invention.

The claimed invention is:

1. A process for separating isoflavones fractions from an aqueous vegetable starting material, said process comprising the steps of:
   (a) heating an aqueous vegetable starting material to a constant temperature selected on a basis of an aqueous solubility for a given isoflavone fractions that is to be recovered;
   (b) passing the heated starting material of step (a) through an ultrafiltration membrane to obtain a permeate, the membrane having a cut-off which passes the given isoflavone fractions;
   (c) adjusting back pressure in a retentate acting on the membrane of step (b) to adjust a flow of said permeate while continuing said ultrafiltration; and
   (d) collecting said isoflavones fractions from the permeate.

2. The process of claim 1 wherein said starting material is soy molasses.

3. The process of claim 2 wherein step (a) includes the further process steps of: making an aqueous ethanol extract of hexane-defatted soybean flakes at a temperature in the range of about 44°–63° C.

4. The process of claim 2 wherein said ultrafiltration of step (b) is carried out within a temperature range of about 65°–95° C.

5. The process of claim 2 wherein the collection of isoflavones fractions from the permeate of step (d) further comprises the steps of:
   (d1) treating the permeate with an adsorptive resin;
   (d2) washing the resin of step (d1) in water; and
   (d3) eluting adsorbed isoflavones fractions from the washed resin of step (d2) with aqueous alcohol.

6. The process of claim 5 wherein step (d3) further comprises the step of:
   (d4) drying the eluted aqueous alcohol of step (d3) to reduce the isoflavones fractions to a solid basis.

7. The process of claim 5 further comprises the step of evaporating the aqeuous alcohol elution of step (d3) to reduce the isoflavones fractions to a solid basis.

8. The process of claim 5 wherein the resin of step (d1) is selected from a group consisting of ionic ethylvinylbenzene-divinylbenzene, non-ionic ethylvinylbenzene-divinylbenzene, ionic styrene-divinylbenzene, non-ionic styrene-divinylbenzene, ionic polystyrene polymers, and non-ionic polystyrene polymers; and the aqueous alcohol of step (d3) is selected from a group consisting of ethanol, methanol, and isopropanol.

9. The process of claim 5 wherein the aqueous alcohol of step (d3) is ethanol.

10. The process of claim 2 wherein the constant temperature of step (a) is in the order of about 65°–95° C.

11. The process of claim 10 wherein said ultrafiltration membrane of step (b) has a nominal molecular weight cut-off range of about 600–100,000.

12. The process of claim 10 wherein said ultrafiltration membrane of step (b) has a nominal molecular weight cut-off range of 10,000 nominal molecular weight.

13. The process of claim 11 wherein the back pressure of step (c) provides a permeate flow in the order of 70 mL/minute.

14. The process of claim 1 further comprising the step of adding water to the retentate of step (b) at a flow rate which is the same as the permeate rate or flux of the permeate, and the step of again passing the permeate with the added water through an ultrafilter.

15. A process of claim 2 further comprising the steps of:
   (e) packing a liquid-chromatography column with a slurry of ethanol with a polymeric resin;
   (f) back flushing the column with water until said resin expands by approximately fifty percent;
   (g) feeding the permeate of step (b) through said column;
   (h) eluting isoflavones fractions from said resin by a use of ethanol; and
   (i) drying the isoflavones fractions eluted in step (h).

16. The process of claim 15 wherein said slurry of step (e) is about 50–100% wt ethanol followed by about 1–5 column volumes of 0.1% wt NaOH and 1–5 column volumes of water.

17. The process of claim 16 wherein the temperature of the permeate during step (g) is about 45°–95° C.

18. The process of claim 15 and a further step after step (g) of washing said resin with water to remove residual sugars and other impurities therefrom.

19. The process of claim 15 wherein said step (i) is a drying step.

20. The process of claim 15 wherein said step (i) is a vacuum drying step.

21. A process for separating isoflavone fraction from an aqueous vegetable starting material, said process comprising the steps of:

ultrafiltrating a heated feed stream of soy molasses starting material to isolate isoflavone fractions in an ultrafiltration permeate;

recovering the isoflavone fractions by adsorption of the permeate on a resin;

washing said resin with water in order to remove residual impurities from the adsorbed isoflavone fractions; and eluting the washed isoflavone fractions with aqueous alcohol.

* * * * *